United States Patent [19]

Oliver et al.

[11] Patent Number: 5,397,353
[45] Date of Patent: Mar. 14, 1995

US005397353A

[54] IMPLANT TISSUE

[76] Inventors: Roy F. Oliver, The University of Dundee, Department of Biological Sciences, The University, Dundee DD1 4HN; Roy A. Grant, Willow Wood, 24 Harbour View Road, Parkstone, Dorset BH14 OPE, both of Great Britain

[21] Appl. No.: 637,172

[22] Filed: Jan. 3, 1991

Related U.S. Application Data

[63] Continuation of Ser. No. 826,482, Jan. 22, 1986, abandoned.

[30] Foreign Application Priority Data

May 24, 1984 [GB] United Kingdom ............... 8413319

[51] Int. Cl.⁶ ............................................... A61F 2/02
[52] U.S. Cl. ...................................... 623/11; 623/66
[58] Field of Search ............... 623/1, 2, 11, 12, 15, 623/16, 66; 424/422, 423; 128/DIG. 8

[56] References Cited

U.S. PATENT DOCUMENTS

| | | |
|---|---|---|
| 3,318,774 | 5/1967 | Dingwall et al. . |
| 3,873,478 | 3/1975 | Comte et al. . |
| 4,060,081 | 11/1977 | Yannas et al. ..................... 623/66 |
| 4,357,274 | 11/1982 | Werner . |
| 4,378,224 | 3/1983 | Nimni et al. . |
| 4,399,123 | 8/1983 | Oliver et al. . |
| 4,420,339 | 12/1983 | Kato ..................................... 623/66 |
| 4,801,299 | 1/1989 | Brendel et al. ....................... 623/1 |

FOREIGN PATENT DOCUMENTS

| | | |
|---|---|---|
| 1317581 | 1/1963 | France . |
| 964545 | 7/1964 | United Kingdom . |
| 995357 | 6/1965 | United Kingdom . |
| 1565340 | 4/1980 | United Kingdom ............ 623/66 |
| 2079797 | 1/1982 | United Kingdom . |

*Primary Examiner*—David Isabella
*Attorney, Agent, or Firm*—Rosenman & Colin

[57] ABSTRACT

A collagenous tissue preparation suitable for homotransplantation or heterotransplantion. The preparation is a non-resorbable, non-antigenic collagenous material which retains the natural structure and original architecture of the natural tissue. The material is substantially free of non-fibrous tissue proteins, glycoproteins, cellular elements and lipids. The tissue preparation is recolonized by host cells and revascularized after implantation into the host.

7 Claims, No Drawings

IMPLANT TISSUE

CROSS-REFERENCE

This is a continuation of Ser. No. 826,482, filed Jan. 22, 1986, now abandoned.

The present invention relates to a new collagenous material which is suitable for homo- or heterotransplantation. It can be used as permanent repair for cutaneous wounds and soft tissue injuries, for the correction of facial and other deformities and for use in general and plastic surgery. The present invention also relates to a process for providing such a material. The material is preferably in the form of a sheet.

In the past, various collagenous preparations have been suggested for the repair of skin wounds and soft tissue injuries. These have comprised dispersions, solutions and gels of collagen, and reconstituted and spongy forms of collagen. These preparations were most often prepared by digesting collagen of animal origin with a proteolytic enzyme active under acidic conditions. The collagenous material is solubilised in the acidic media and can be filtered from any debris and insoluble skin components. The solubilised collagen may be reconstituted as a solid, gel or sponge by raising the pH of the solution and stabilising by cross-linking. However, the natural structure of the collagen is lost in this process. The resulting preparations tend to have little or no tensile strength, are amorphous in structure and show a propensity for being reabsorbed, either disappearing from the site of injection or implantation or being replaced by scar tissue. It is now believed that one of the skin components which is separated from the collagen in many prior art processes is elastin. It is now believed that elastin can play a useful part in the successful use of fibrous collagenous material derived from skin. The fibrous tissue of the invention-normally retains elastin. The collagenous material of the fibrous tissue can comprise up to about 15% by weight of elastin but more usually contains 1 to 5%. The elastin is present as fibres which retain their natural conformation within the tissue.

A different class of collagenous materials are those in which the basic structure of the natural collagen (for example from skin) is maintained. British Patent Specification No. 1565340 describes and claims a process for treating fibrous tissue of human or animal origin to provide a fibrous tissue preparation which is suitable for heterotransplantation, which process comprises treating the fibrous tissue with two enzymes, one of said enzymes being a proteolytic enzyme which will under the conditions of the process remove non-fibrous tissue proteins, and the other of said enzymes being a carbohydrate-splitting enzyme which will under the conditions of the process remove antigenic polysaccharide, mucopolysaccharides and glycoproteins from the tissue. This process yielded a collagenous material that was stable and strong. We have now found that this process described therein can be improved and that the resulting preparations have unexpected benefits. The process improvements include:

A. The amount and composition of mucopolysaccharides found in animal tissues is very variable (generally they only contain small amounts, but some tissues such as arteries may contain a greater percentage). Moreover, compared with glycoproteins mucopolysaccharides are less antigenic and some may be non-antigenic. Proteolytic enzyme treatment splits glycoproteins into carbohydrates and peptides which rapidly defuse out of the tissue. Hence, when only small amounts of mucopolysaccharides are present (for example in the dermis) or where they are not demonstrably antigenic then it may not be necessary to treat the tissue with a carbohydrate-splitting enzyme. A single-enzyme treatment with the proteolytic enzyme will lead to an implantable preparation. This particularly aids in preparation of the fibrous tissue of the invention when derived from materials such as the dermis.

B. While the preparation of British Patent Specification No. 1565340 generally shows little degenerative changes with time following implantation in animals or man, spontaneous calcification has been found to occur in the implanted tissue either in small foci or over larger areas. While such calcification is not toxic to the animal, the accompanying loss of flexibility in the implant is a disadvantage and reduces its value as a replacement or repair. We now believe that this calcification is in some way related to the presence in the tissue of lipids and their association material. By removal of these lipid portions from the tissue, we find that the occurrence of calcification can be significantly reduced. One method of removing these portions is by the use of a selective enzyme such as lipase. A further, simpler and preferred method is solvent extraction using an organic solvent. Particularly suitable solvents are acetone, ethanol, ether, or a mixture thereof. The finding that lipid removal, particularly with the simple step of solvent extraction, results in implantable material which is resistant to calcification is of great importance from a practical clinical point of view, and greatly enhances the medical value of such preparations if they are to be used in general and plastic surgery in man.

C. British Patent Specification No.1565340 discloses the use of certain chemical compounds to remove residual antigenicity from the preparations, and to stabilize them against break-down due to attack of endogenous proteolytic enzymes following implantation. The particular compounds referred to in the Patent are aldehydes, sulphones and cyanuric chloride of which aldehydes being the preferred class. Aldehydes and the other compounds mentioned have been found to be toxic to cells and living tissue, and it has been found difficult to remove all traces of the compounds from the known preparations. Following implantation, the presence of residual toxic material is sometimes indicated by infiltration of lymphocytes and giant cells at the site of the implant. Moreover, the prolonged washing with saline or buffer solution to remove residual compounds from the known preparation is a disadvantage from a practical point of view.

It has been found unexpectedly that treatment of the preparation with polyisocyanates such as diisocyanate cannot only confer stability against attack by endogenous proteolytic enzymes such that they do not break down and become reabsorbed following implantation in animals, but can also result in the preparations having little or no propensity to be cytotoxic when implanted. This is in contrast to aldehyde treated preparations where residual cytotoxicity may be found. This finding is of great importance from a clinical point of view where inertness of the preparation over long periods is needed. A further advantage is that collagenous preparations stabilised with diisocyanates can be white in colour as compared with the "khaki" tint of aldehyde-treated preparations, which may be cosmetically desirable.

It is a further advantage that in this process the original architecture of the collagenous fibrous material is preserved. The material is neither solubilised or denatured in the process so its natural structure is maintained which makes an implant derived from the material feel natural rather than an inert material and gives the implant a permanency which has been lacking in several previously commercialised implant materials.

In accordance with one aspect of the present invention there is provided a substantially non-antigenic fibrous tissue preparation of human or animal origin which is suitable for homo- or heterotransplantation as a permanent repair for cutaneous and soft tissue injuries which preparation is substantially free of non-fibrous tissue proteins and glycoproteins, is non-cytotoxic, substantially free of cellular elements, and substantially free of lipids and lipid residues.

Clearly this aspect of the invention may be written in alternative form as the present invention provides a substantially non-antigenic fibrous tissue preparation of human or animal origin which is suitable for homo- or heterotransplantation as a permanent repair for cutaneous and soft tissue injuries, which preparation is substantially free of non-fibrous tissue proteins and glycoproteins and substantially free of cellular elements characterised in that the preparation is substantially free of lipids and lipid residues and is non-cytotoxic.

Non-fibrous tissue proteins and glycoproteins include globular proteins and the like. Cellular elements as well as comprising hair follicles and sweat glands can include any antigenic proteins and enzymes and other cellular debris arising from the processing conditions.

Those substances said to be "substantially free" of materials generally contain less than 5% of and preferably less than 1% of said materials.

In another aspect this invention provides a process for treating fibrous tissue of human or animal origin to provide a fibrous tissue preparation which is suitable for homo- or heterotransplantation which process comprises treating the fibrous tissue to remove therefrom substantially all lipids and lipid residues, and thereafter treating the tissue with a proteolytic enzyme which will under the conditions of the process remove non-fibrous tissue proteins and glycoproteins from the tissue.

In an additional aspect the invention also provides a process for stabilizing and simultaneously removing residual antigenicity from a fibrous tissue preparation of human or animal origin which is suitable for homo- or heterotransplantation, which process comprises treating the preparation with polyisocyanate and preferably with a diisocyanate.

Suitably the polyisocyanate used will be capable of reacting with the amino and hydroxyl groups of protein chains of the collagenous material. The polyfunctional isocyanates will react with or cross-link amino or hydroxyl groups of different protein chains so forming a material which has a stable structure retaining the original architecture of the collagen and which is resistant to enzymatic attack. It is known that antigenicity is associated with the amino groups of the protein chains of collagenous material, reacting these amino groups with isocyanate removes any antigenicity associated with these groups.

Preferred polyisocyanates are diisocyanates which include aliphatic, aromatic and alicyclic diisocyanates as exemplified by 1,6-hexamethylene diisocyanate, toluene diisocyanate, 4,4'-diphenylmethane diisocyanate, and 4,4'-dicyclohexylmethane diisocyanate, respectively. The preferred diisocyanate is hexamethylene diisocyanate (HMDI).

Further evidence of the low cytotoxic nature of the new material is demonstrated by the finding that both human skin fibroblasts and dispersed rat epidermal cells will grow on it under tissue culture conditions. This has important clinical implications in such areas as skin reconstruction.

Preferably the preparation of this invention is in sheet form and most preferably is derived from the dermis of animals such as the pig or cow, of which pig dermis is preferred.

In a favoured aspect this invention provides an implant for the permanent repair of cutaneous or soft tissue injuries in humans which comprises a sheet of fibrous collagenous tissue derived from dermis which implant is substantially non-antigenic, and substantially free of non-fibrous tissue proteins, glycoproteins and cellular elements characterised in that the implant is non-cytotoxic and substantially free of lipids and lipid residues.

Most favourably the implant is derived from pig dermis.

Suitably the fibrous collagenous tissue will have a thickness of from 0.25 to 5 mm, more suitably will have a thickness of 0.5 to 4 mm and preferably will have a thickness of 1.0 to 3 mm, for example 1.5 mm, 2.0 mm, 2.5 mm and 3.0 mm.

The size of the fibrous collagenous tissue in terms of width and length will vary according to the size of the repair but usually the size range will vary from 1 cm×1 cm to 12 cm×12 cm but strips from 10 to 30 cm×1 to 5 cm may also be used, for example in some hernioplasty implants. More suitably the size will vary from 2 cm×2 cm to 10 cm×10 cm and preferably from 2 cm×2 cm to 8 cm×8 cm, for example 2 cm×2 cm, 3 cm×3 cm, 2 cm×4 cm, 3 cm×7 cm, 6 cm×8 cm and 8 cm×8 cm.

The new collagenous sheet material is stable and can be stored for long periods either deep frozen or freeze-dried, or as a wet preparation in the presence of a bactericide or in an organic solvent such as-acetone. Preparations may be sterilized by gamma irradiation or hydrogen peroxide for example, and then packed sterile in a bacteria-proof package.

A preferred method of preparation of the new material is as follows:

(a) Freshly cut dermis is extracted with acetone with one or more changes.

(b) The dermis is placed in buffer or saline solution to remove the acetone.

(c) The dermis is then subjected to digestion with trypsin solution pH 7.0 to 9.0 to remove antigenic proteins and cellular elements such as hair follicles and sweat glands.

(d) Optionally the tissue may be treated with a carbohydrate-splitting enzyme such as amylase, hyaluronidase or neuramidase to remove antigenic polysaccharides and mucopolysacchardies.

(e) The purified tissue is stabilised by treatment with a diisocyanate e.g. hexane diisocyanate as a 0.1% solution in acetone.
(f) Two further washes with acetone.
(g) Rinse with buffer or saline.
(h) Store in presence of a bactericide or sterilize with gamma irradiation.
(i) Pack under sterile conditions.

Other tissues can be processed in a like manner.

When implanted subcutaneously the new collagenous sheet material become recolonized by host cells and revascularized. This is of great clinical importance as it allows for long term use. The material has been found not to elicit immunological reactions in animals and, when removed by biopsy at varying intervals of time, showed no evidence of degeneration or calcification. Furthermore, in tissue culture the new material was found to become covered with a structural epidermis when small pieces of split thickness skin were placed in it, and when implanted into skin wounds it became overgrown with epidermis and eventually appeared as normal skin apart from the absence of hairs. This is in contrast with tissue treated with the cross-linking and stabilizing agents of UK Patent Specification 1,565,340. The collagenous sheet material of this invention has been found to inhibit the contraction of some full thickness skin wounds and help suppress the formation of granulation tissue in such wounds. This latter property is important in that it tends to prevent the formation of scar tissue.

In order that the invention may be more fully understood, the following Example is given by way of illustration only.

EXAMPLE 1

Suitably cut pig dermis was immersed in acetone. After 1 hour, the acetone was removed and replaced by fresh. After a further hour, the dermis was removed from the acetone and placed in 0.1M phosphate buffer pH 9.0 to extract residual acetone. The dermis was then digested with a solution of crystalline trypsin at a concentration of 2 mg/ml in 0.1M phosphate buffer with 0.5 mg/ml sodium azide as a bactericide at 15° C. for 28 days. The purified tissue was removed from the trypsin solution, rinsed in buffer, excess solution removed and placed in a 0.1% solution of hexane diisocyanate in acetone. After 9 hours the tissue was removed from the diisocyanate solution and rinsed with two changes of acetone followed by two changes of buffer. The resulting preparation which was white in colour was implanted subcutaneously into inbred Porton rats (PVG/C). Subsequent biopsies at 7, 14 and 28 days and 3 and 6 months showed that the implanted material became infiltrated with host fibroblasts and was revascularized. There was no evidence of lymphocyte infiltration or giant cell formation in the implant nor any sign of calcification in the implant.

Strips of the preparation were placed in a suspension of human fibroblasts in tissue culture medium and maintained at 37° C. After a suitable interval 5 days the preparation was removed from the medium and examined histologically. It was found to be covered with a layer of fibroblasts and in addition other fibroblasts had migrated into the tissue matrix thus demonstrating the non-cytotoxicity of the preparation to human fibroblasts.

Also, when-small pieces (0.2×0.2 cm.) pieces of split-thickness rat skin were explanted onto pieces of the new material measuring 1×1 cm, or when dispersed epidermal cells were placed onto the new material, complete coverage with layered epithelium occurred with 8–9 days by epidermal cell migration and proliferation from the explants.

The new collagenous sheet material will be suitable for use in human and veterinary surgery for the treatment of hernias, skin wounds including burns, correction of facial deformities, tendon damage, in various arthroplastics and generally in plastic and reconstructive surgery.

EXAMPLE 2

Suitably cut pig dermis was immersed in acetone. After 1 hour, the acetone was removed and replaced by a second portion of acetone. After a further hour, the dermis was removed from the acetone and placed in 0.1M phosphate buffer pH 7.0 to extract residual acetone. The dermis was then digested with a solution of crystalline papain at a concentration of 3 mg/ml in 0.1M phosphate buffer with 0.01M cysteine as activator and 0.5 mg/ml sodium azide as a bactericide at 15° C. for 28 days. The purified tissue was removed from the papain solution, rinsed in buffer, excess solution removed and placed in a 0.1% solution of hexane diisocyanate in acetone. After 9 hours the tissue was removed from the diisocyanate solution and rinsed with two changes of acetone followed by two changes of buffer. The resulting preparation which was white in colour was implanted subcutaneously into inbred Porton rats (PVG/C). Subsequent biopsies at 3 and 6 months showed that the implanted material became infiltrated with host fibroblasts and was revascularised. There was no evidence of lymphocyte infiltration or giant cell formation in the implant nor any sign of calcification in the implant.

It was found that human fibroblasts in tissue culture medium grew to cover the preparation after an interval of 5 days.

Also, when small pieces (0.2×0.2 cm) pieces of split-thickness rat skin were explanted onto pieces of the preparation measuring 1×1 cm, or when dispersed epidermal cells were placed onto the new preparation, complete coverage with layered epithelium occurred within 8–9 days by epidermal cell migration and proliferation from the explants.

EXAMPLE 3

The stratum corneum is removed from pig skin using a dermatome. The remaining skin tissue, the dermis, is cut into pieces 4 cm×1 cm and sectioned into 0.2 cm thick strips using a dermatome. These pieces are extracted in acetone employing three 1 hour extractions and one 36 hour extraction. The ratio of tissue to acetone for each extraction is 1:5 (w/v). The pieces of dermis are then washed several times in sterile saline to remove acetone. The washed pieces are incubated with trypsin in sterile sodium phosphate buffer 0.1M pH 8.0 containing sodium chloride at 0.9% (w/v) and sodium azide (0.5 g/l) employing 100 g trypsin per 2 liters of buffer. The trypsin digestion is performed for 7 days and the fluid is decanted. The tissue pieces are washed several times in saline. The pieces of tissue are then inspected and any residual hairs are removed by use of forceps. The dehaired pieces are washed and are subjected to a second trypsin digestion for 21 days. At the end of this period the fluid is decanted and the pieces are washed with sterile saline, several times with a final wash of 20 hours. The wet tissue pieces are dehydrated using acetone by laying the tissue flat in a polypropylene tray and immersing it in acetone. The dehydrated tissue is rigid and is transferred to a screw capped bottle and washed twice more with acetone. The acetone-washed pieces are then treated with a solution of hexamethylene diisocyanate (HMDI) in dry acetone 0.01% w/v) treating 250 g of tissue with 5 liters of solution. The treatment period is 20 hours (approximately). The pieces of tissue are then washed with wet acetone, four times for 1 hour and a final wash of 20 hours. The tissue pieces are then washed free of acetone using sterile saline, twice for 1 hour and a final wash of 20 hours.

The fibrous tissue preparation so formed is stored immersed in sterile phosphate buffer 0.1M, pH 7.2 containing sodium azide.

The fibrous tissue preparation may be sterilised by gamma-irradiation and may be used for heterotransplantation.

(Like other collagenous materials of the invention this fibrous tissue preparation consists essentially of collagen with small proportions of elastin).

We claim:

1. A non-resorbable, substantially non-antigenic collagenous fibrous tissue preparation of human or animal tissue origin, which is suitable for homo- or heterotransplantation as a permanent repair for cutaneous wounds and soft tissue injuries, which preparation retains the natural structure and original architecture of said human or animal tissue, is substantially free of non-fibrous tissue proteins and glycoproteins, is substantially free of cellular elements, is substantially free of lipids and lipid residues and is non-cytotoxic, wherein said preparation is capable when implanted of being recolonized by host cells and revascularized while being resistant to calcification.

2. A preparation as claimed in claim 1 additionally substantially free of antigenic polysaccharides and mucopolysaccharides.

3. A preparation as claimed in any one of the preceding claims when in the form of a sheet.

4. An implant for the permanent repair of cutaneous or soft tissue injuries in humans which comprises a sheet of substantially non-antigenic collageneous fibrous tissue preparation of claim 1.

5. An implant as claimed in claim 4 in which the implant is derived from pig dermis.

6. An implant as claimed in either of claims 4 or 5 in which the implant is formed from a sheet of fibrous collagenous tissue which has been cross-linked by means of a polyisocyanate.

7. An implant as claimed in claim 6 in which the polyisocyanate is hexamethylene diisocyanate.

* * * * *